United States Patent [19]

Weiss et al.

[11] 4,296,071

[45] Oct. 20, 1981

[54] PIPETTE WITH ELASTIC BELLOWS

[75] Inventors: Erich Weiss, Mannheim-Sandhofen; Dieter Ungermann, Mannheim, both of Fed. Rep. of Germany

[73] Assignee: Boehringer Mannheim, Mannheim-Waldhop, Fed. Rep. of Germany

[21] Appl. No.: 94,134

[22] Filed: Nov. 14, 1979

[30] Foreign Application Priority Data

Nov. 29, 1978 [DE] Fed. Rep. of Germany ....... 2851532

[51] Int. Cl.³ ........................ B01L 3/02; G01N 1/14; A61M 1/00

[52] U.S. Cl. .............................. 73/864.11; 73/864.18; 128/230; 128/232; 128/765; 422/100

[58] Field of Search ........................ 73/425.6, 425.4 P; 141/27; 222/309, 209, 401; 128/231-233, 218 R, 765; 401/153; 422/100

[56] References Cited

U.S. PATENT DOCUMENTS

| | | | |
|---|---|---|---|
| 2,595,493 | 5/1952 | Slaby et al. | 422/100 |
| 3,340,869 | 9/1967 | Bane | 128/765 |
| 3,810,391 | 5/1974 | Suovaniemi | 73/425.6 |
| 4,096,750 | 6/1978 | Sturm | 73/425.6 |

FOREIGN PATENT DOCUMENTS

| | | | |
|---|---|---|---|
| 1032326 | 7/1953 | France | 401/153 |
| 449894 | 7/1949 | Italy | 222/209 |

*Primary Examiner*—William F. Smith
*Assistant Examiner*—Chris Konkol
*Attorney, Agent, or Firm*—Sprung, Felfe, Horn, Lynch & Kramer

[57] ABSTRACT

Pipette with elastic bellows wherein the travel of the bellows is limited by preset stops. The bellows is prestressed between the stops over a range of movement within which the bellows possesses adequate spring-back force to return to a rest position predetermined by one of the stops.

8 Claims, 2 Drawing Figures

PIPETTE WITH ELASTIC BELLOWS

BACKGROUND

This invention relates to a pipette with an elastic bellows.

For the pipetting of accurate volumes, plunger pipettes are generally used. However, their manufacturing cost is rather high because they require a close-fitting plunger/barrel arrangement.

From German patent application DE-AS No. 12 74 282, simple bellows syringes are known which are intended for injections. However, they cannot be used to draw up and deliver accurately measured volumes of liquid.

The use of a bellows in the mouthpiece of a pipette has also been proposed (U.S. Pat. No. 3,343,422). In this prior-art arrangement, the bellows is provided to protect the user against the inhalation of noxious vapors and liquids. However, like bellowless pipettes generally, this arrangement has the drawback that the accuracy of volume determination is largely dependent on the skill of the user. The pipetting of accurate volumes there is difficult and time-consuming.

SUMMARY

The invention provides a pipette whose accuracy in use is comparable to that of pipettes with a plunger/barrel arrangement but which can be produced much more cheaply. The pipette is to be so easy to use that it can be used even by a layman to reliably pipette accurate amounts of liquid.

This is accomplished in a pipette where one end of the bellows is fixed and the travel of the other end of the bellows is limited by preset stops. Over the range in which it possesses adequate springback force, the bellows is prestressed between the stops such that it will return without external aids to a rest position predetermined by one of the stops.

Actual tests performed with the pipette in accordance with the invention have shown that the bellows will work with considerably greater accuracy than hitherto achieved if it is confined to the range of movement between stops located outside the marginal regions. It has been found that the range of movement or working range of the bellows should be at least 5 percent, and preferably 20 percent, smaller than its maximum possible range of movement. This insures accuracy and compensates for manufacturing tolerances.

The pipette can be produced at a considerably smaller cost than other devices of comparable accuracy.

Advantageous variants of the invention will become apparent from the dependent claims and are described in greater detail below with reference to a drawing which diagrammatically illustrates an embodiment.

DESCRIPTION

Figure 1:
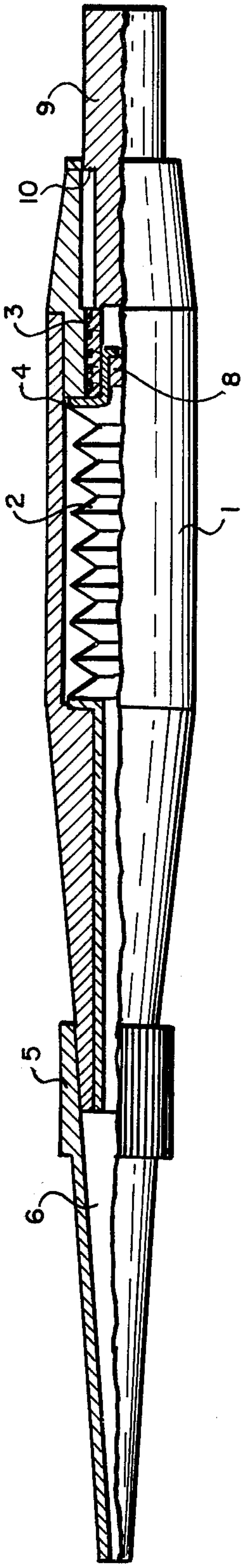
FIG. 1 of the drawing shows a longitudinal section through a pipette comprising a shell 1 with internal bellows 2.
Figure 2:
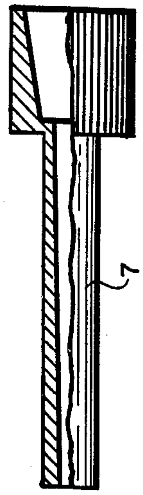
FIG. 2 shows an alternate construction for the syringe portion of the pipette.

The shell 1 is constructed as a grip in which stops 3 and 4 are provided for limitation of the travel of the bellows 2. The mouth 5 of the bellows projects slightly beyond the shell 1, which at that point is a tight fit. Interchangeable suction syringes 6 and 7 may be set onto that mouthpiece 5, depending on the particular use.

The material of which the bellows 2 is made is so elastic that the bellows can be compressed from the end of the cylinderical portion 8 which is opposed to the suction opening, and will again springback or expand to its original length when the actuating pressure is removed.

There are bellows of relatively high elasticity. However, their elasticity is not linear throughout their length. Conventional bellows pipettes are inaccurate mainly because they lack a reproducible rest position. In the pipette of the invention, the rest position of the bellows 2 is preset by the stop 4 in order to avoid the range of inaccuracy. Stop 4 in conjunction with stop 3 defines precisely and reproducibly the travel of the bellows.

Since the restoring force of any bellows is a function of the weight of liquid to be drawn up and of the ageing of the material of construction, a return spring (not shown in the drawing) may in principle be provided to support the elasticity of the bellows.

The likewise deformable slip-on syringes are designed so that they are held to the suction opening by pressure alone. To secure them in position, projections may be provided at the suction opening 5, and recesses in the opposed inner region of the suction syringes 6 and 7, so that the latter are able to snap onto the pipette. Other syringes which can readily and quickly be detached are conceivable but are not shown for the sake of clarity.

The bellows 2 can project from the grip 1 by a cylindrical portion which may serve as a pushpin. In the embodiment illustrated, the cylindrical portion 8 is covered by a slip-on cap 9 which interlocks therewith and thus making the two movable together. The cap may be provided with elevations 10 and may be made of a material that is harder than the bellows 2 so as to define the travel of the bellows 2 still more sharply when slipped onto the cylindrical end of the bellows.

For adjustment of the travel of the bellows, one of the stops is advantageously constructed as a threaded member which can be turned in a screw thread in the grip 1 so as to either compensate for differences in manufacturing tolerances or to calibrate the pipette for different amounts of liquid. However, the adjustment of a stop 3 or 4 is limited to the range over which the bellows extends prestressed in the grip 1, for the reasons outlined.

It will be appreciated that the instant specification and claims are set forth by way of illustration and not limitation, and that various modifications and changes may be made without departing from the spirit and scope of the present invention.

What is claimed is:

1. A pipette comprising: an elongated casing; an elastic bellows disposed in the casing with one end thereof fixed to the casing; and means mounting the other end of the bellows for longitudinal movement relative to the casing from a rest position to a predetermined compressed position and wherein the bellows is prestressed over the entire range of travel between the rest and compressed positions and has sufficient elasticity to return to the rest position unaided, the mounting means comprising stop means forming two separate stops limiting movement of the other end of the bellows wherein one stop defines the rest position and the other stop defines the compressed position.

2. Pipette of claim 1 wherein the other end of the bellows is cylindrical and constructed as a pushpin.

3. Pipette of claim 2 further comprising cap means configured to connect by interlocking engagement to the cylindrical portion of the bellows.

4. Pipette of claim 3 wherein the cap means has at least one radial surface for operatively engaging with the stop means to define the compressed position.

5. Pipette of claim 1 wherein the stops comprise part of the casing.

6. Pipette of claim 1 wherein the range of movement of the bellows means is reduced by the stops by at least 5 percent of its possible maximum range of movement.

7. Pipette of claim 1 having an interchangeable suction syringe.

8. Pipette of claim 6 wherein the range of movement of the bellows means is reduced by the stops by at least 20 percent of its possible maximum range of movement.

* * * * *